US012708312B2

(12) United States Patent
Dreisbach et al.

(10) Patent No.: US 12,708,312 B2
(45) Date of Patent: Aug. 18, 2026

(54) SYSTEM AND METHOD FOR SCALABLE ECG ANALYSIS

(71) Applicant: Bardy Diagnostics, Inc., Bellevue, WA (US)

(72) Inventors: Ezra Dreisbach, Vashon, WA (US); Daniel Paris, Issaquah, WA (US)

(73) Assignee: Bardy Diagnostics, Inc., Bellevue, WA (US)

( * ) Notice: Subject to any disclaimer, the term of this patent is extended or adjusted under 35 U.S.C. 154(b) by 290 days.

(21) Appl. No.: 18/419,023

(22) Filed: Jan. 22, 2024

(65) Prior Publication Data

US 2024/0252092 A1 Aug. 1, 2024

Related U.S. Application Data

(60) Provisional application No. 63/441,915, filed on Jan. 30, 2023.

(51) Int. Cl.
*A61B 5/349* (2021.01)
*A61B 5/00* (2006.01)
*A61B 5/308* (2021.01)

(52) U.S. Cl.
CPC ............ *A61B 5/349* (2021.01); *A61B 5/0006* (2013.01); *A61B 5/308* (2021.01); *A61B 5/746* (2013.01)

(58) Field of Classification Search
CPC ....... A61B 5/349; A61B 5/308; A61B 5/0006; A61B 5/746
See application file for complete search history.

(56) References Cited

U.S. PATENT DOCUMENTS

2019/0357794 A1* 11/2019 Bardy .................. A61B 5/7203
2022/0223274 A1* 7/2022 Bardy ..................... H04L 67/12
2022/0263835 A1* 8/2022 Pieczul ................... H04L 63/20
(Continued)

OTHER PUBLICATIONS

Fan Xiaomao et al. "Toward Automated Analysis of ECG Big Data by Graphics Processing Unit for Mobile Health Application", IEEE Access, vol. 5, pp. 17136-17148, XP011660526, DOI: 10.1109/Access.2017.2743525. Retrieved on Sep. 14, 2017. (Year: 2017).*
(Continued)

*Primary Examiner* — Frantz B Jean
(74) *Attorney, Agent, or Firm* — K&L Gates, LLP.

(57) ABSTRACT

The efficient utilization is provided within a cloud-computing environment where a master plane executing on a master node controls spinning up and down worker nodes, with worker nodes whose output is necessary for functioning of other worker nodes being spun up before the worker nodes needing that output. By dedicating the available computational resources to the earlier-spun worker nodes, these worker nodes are able to process a greater amount of monitoring data. Once the output of these worker nodes is ready, the available resources are reallocated to the worker nodes that use the output of the earlier-spun worker nodes. Additional control over the cardiac monitoring can be provided by communicating with a monitor to increase the rate at which the monitor transmits the collected data as well as pausing generation of alerts based on the monitoring data if such alerts are likely to be inaccurate.

19 Claims, 6 Drawing Sheets

(56) References Cited

U.S. PATENT DOCUMENTS

| | | | | |
|---|---|---|---|---|
| 2023/0109648 | A1* | 4/2023 | Sipe | A61N 1/046 607/5 |
| 2024/0108290 | A1* | 4/2024 | Jeon | A61B 5/0022 |

OTHER PUBLICATIONS

Cheikhrouhou et al. "One-Dimensional CNN Approach for ECG Arrhythmia Analysis In Fog-Cloud Environments", IEEE Access, IEEE, USA, vol. 9, Jul. 16, 2021 (Jul. 16, 2021), pp. 103513-103523.

Fan et al: "Toward Automated Analysis Of Electrocardiogram Big Data By Graphics Processing Unit For Mobile Health Application", IEEE Access, vol. 5 , pp. 17136-17148.

Iftikhar et al. "Fogdlearner: A Deep Learning-Based Cardiac Health Diagnosis Framework Using Fog Computing", Proceedings of The 1 St Conference on Mile-High Video, Acmpub27, 2022 pp. 136-144.

International Search Report and Written Opinion for International Application No. PCT/US2024/012411, dated May 27, 2024.

International Preliminary Report on Patentability for International Application No. PCT/US2024/012411, dated Jul. 31, 2025.

* cited by examiner

10
CPU Node
Input Service
Main Service
BDBD
PVC PAC
LXA Cnvrtr.
Report GNTR.
Database
Monitoring Data
Reports
Output
GPU Node
Noise Dtctr.
Afynd
Master Node
Control Panel
Network (53)

120
Control alert processing during monitoring
Receive monitoring data that includes actigraphy data
121
Alert Necessary?
122
No
Yes
Generate alert
123
Alert False?
124
No
Yes
125
Provide alert
Pause alert generation
126
127
Additional monitoring data received?
Yes
No
Pause Active?
Yes
No
128
End

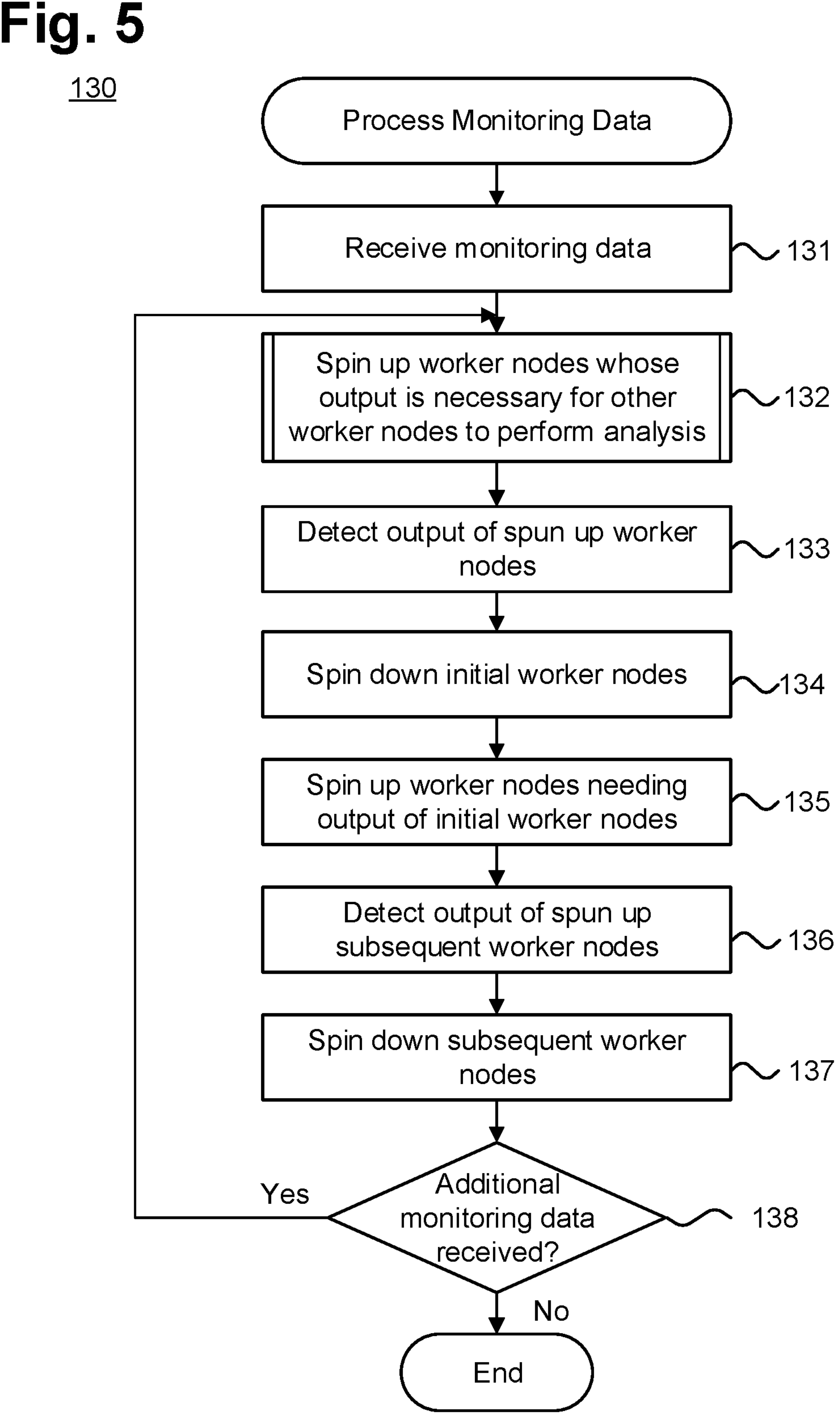
Fig. 5
130
Process Monitoring Data
Receive monitoring data
131
Spin up worker nodes whose output is necessary for other worker nodes to perform analysis
132
Detect output of spun up worker nodes
133
Spin down initial worker nodes
134
Spin up worker nodes needing output of initial worker nodes
135
Detect output of spun up subsequent worker nodes
136
Spin down subsequent worker nodes
137
Additional monitoring data received?
138
Yes
No
End

SYSTEM AND METHOD FOR SCALABLE ECG ANALYSIS

CROSS-REFERENCE TO RELATED APPLICATION

This application claims the benefit of U.S. Provisional App. 63/441,915, filed Jan. 30, 2023, titled SYSTEM AND METHOD FOR SCALABLE ECG ANALYSIS, the disclosures of which are incorporated by reference herein in their entirety and relied upon.

FIELD

This application relates in general to cardiac monitoring and, in particular, to a system and method for scalable ECG analysis.

BACKGROUND

Patient physiology is one of the four cornerstones of modern diagnostic medicine, which defines the structured process routinely employed by physicians and other medical professionals (henceforth, simply "physicians") to determine the nature and cause of patient health concerns and problems, and physicians need data on patient physiology that is timely, accurate, and reliable to provide effective health care. Through the diagnostic medicine process, a physician will make findings of possible diagnoses that can explain or match a patient's signs and symptoms in terms of a disease or medical condition, which thereby enables the physician to formulate a plan of treatment and follow-up care. The determination of patient physiology is particularly important in the case of cardiac conditions, where electrocardiographic ("ECG") monitoring can provide a wealth of valuable diagnostic information regarding presence and severity of cardiac conditions, including rhythm disturbances (such as atrial fibrillation and ventricular tachycardia), electrolyte disturbances (such as hypokalemia and hyperkalemia), coronary artery blood flow disturbances (such as myocardial infarction and myocardial ischemia), heart block, as well as structural abnormalities.

While the final diagnosis is generally made by a physician, the analysis of the data resulting from an ECG monitoring on which the physician bases the diagnosis is often automated to increase the rate at which patients can be diagnosed. However, the use of the computer-based ECG data processing faces multiple challenges that affect the processing's efficacy. First, as the number of patients in need of cardiac diagnosis performed by a single ECG data processing system grows, the available computational resources of that system may not be sufficient to process the monitoring data for all of the patients at the same time, causing delays in diagnosis that could be especially undesirable when a patient is experiencing an acute cardiac condition. The computational resource shortage can further be exacerbated when the ECG data needs to be subjected to multiple types of analysis, with each type of analysis requiring computational resources. While one approach to solving this challenge would be to buy additional computational resources, such an approach may take substantial time to implement and also comes with a not-inconsiderable cost, thus raising barriers to receiving cardiac care.

A further challenge facing ECG data computer-based processing solutions is particularly apparent when the solutions are used to analyze data gathered through ambulatory ECG monitoring. Whereas inpatient ECG monitoring is generally conducted for a short time and by trained medical personnel who can adjust the parameters of the monitoring if required, inpatient monitoring is often incapable of capturing sporadic cardiac conditions that do not manifest at the time the monitoring is performed. Instead, ambulatory monitors, such as cutaneous or implantable cardiac monitors are used to diagnose such conditions. However, the parameters of operation of ambulatory monitors are generally preset before or at the time of dispatch to the patient, and the data is received from such monitors at whatever intervals are preprogrammed into those monitors. For some monitors, the data is received only following a completion of the monitoring, thus being of no use in real-time assessment of the patient at the time of the monitoring. For those monitors that do offload data prior to the completion of the monitoring, the ambulatory data is offloaded at a predefined frequency. When a patient is experiencing an acute cardiac condition in diagnosing which the monitoring data would be useful, such frequency could be insufficiently low. On the other hand, when the patient's physiology is atypical due to an activity the patient is engaging in (such as physical exercise) as opposed to experiencing an episode of a cardiac condition, that predefined frequency can create false alarms that consistently require attention of medical personnel, thus increasing the time that these medical personnel need to provide diagnosis for other patients.

Accordingly, there is a need for a way to efficiently manage computational resources used for processing cardiac monitoring data as well as adjust for inadequacies of the preset data transmission rate of cardiac monitors.

SUMMARY

The number of patients whose monitoring data is processed at the same time can be scaled up through efficient utilization of computational resources. The efficient utilization is provided within a cloud-computing environment where a master plane executing on a master node controls spinning up and down worker nodes, with worker nodes whose output is necessary for functioning of other worker nodes being spun up before the worker nodes needing that output. By dedicating the available computational resources to the earlier-spun worker nodes, these worker nodes are able to process a greater amount of monitoring data in a certain time period. Once the output of these worker nodes is ready, the available resources are reallocated to the worker nodes that use the output of the earlier-spun worker nodes, also allowing these nodes to process a greater amount of data in a certain time period. Additional control over the cardiac monitoring can be provided by communicating with a monitor to increase the rate at which the monitor transmits the collected data to the cloud-computing environment as well as pausing of generation of alerts based on the monitoring data if such alerts are likely to be inaccurate.

In light of the disclosure set forth herein, and without limiting the disclosure in any way, in a first aspect of the present disclosure, which may be combined with any other aspect, or portion thereof, a system for scalable ECG analysis is provided. The system includes a plurality of nodes. The one or more of the nodes are executed by at least one of one or more CPUs and one or more GPUs.

The plurality of nodes further include a plurality of worker nodes and a master node. Each of the plurality of worker nodes include at least one pod associated with an address. Each pod includes one or more containers. Each container includes a run-time environment in which one or more ECG analysis applications are executed and associated with computational resources.

The master node includes a control plane configured to spin up and spin down the worker nodes, wherein spinning up the worker nodes uses the computational resources. The master node is further configured to coordinate instantiation and lifecycle of the pods, which includes coordinating execution of the ECG analysis applications associated with the worker nodes, including spinning up the nodes whose output is needed by other ones of the nodes before spinning up the other nodes needing the output, receiving a message regarding completion of the output, and spinning up the other nodes needing the output. Spinning up the other nodes after spinning up the nodes producing the output conserves the computational resources and allows to increase a number of the nodes producing the output that are spun up.

In a second aspect of the present disclosure, which may be combined with any other aspect, or portion thereof, the nodes associated with those of the ECG analysis applications utilizing artificial intelligence are executed by of the one or more of the GPUs.

In a third aspect of the present disclosure, which may be combined with any other aspect, or portion thereof, the pods communicate with each other via a queuing service.

In a fourth aspect of the present disclosure, which may be combined with any other aspect, or portion thereof, spinning down one of the pods includes retaining connection of the node associated with that pod to GPU or CPU executing the node.

In a fifth aspect of the present disclosure, which may be combined with any other aspect, or portion thereof, the ECG analysis applications include a beat detector application, a noise detection application, an atrial fibrillation detection application, a premature ventricular contraction detection application, file conversion application for third party analysis applications, and a file combining application that combines the output of other ones of the applications.

In a sixth aspect of the present disclosure, which may be combined with any other aspect, or portion thereof, the nodes associated with the beat detector application and the noise detection application are spun up before the nodes associated with the atrial fibrillation detection application, the premature ventricular contraction detection application, the file conversion application, and the file combining application.

In a seventh aspect of the present disclosure, which may be combined with any other aspect, or portion thereof, the system further includes a cardiac monitor having at least one pair of ECG sensing electrodes; an ECG front end circuit interfaced to a microcontroller and configured to capture cardiac action potentials sensed by the pair of ECG sensing electrodes, which are output as ECG signals; a wireless transceiver interfaced to the microcontroller; and a memory interfaced to the microcontroller. The microcontroller is operable to execute under micro programmable control and is configured to sample the electrocardiographic signals, to store each of the samples into the memory, and to transmit using the wireless transceiver to a server those of the samples that have not previously been transmitted to the server at a predefined frequency.

The system further includes one or more of the applications on one or more of the worker nodes configured to receive a request for a real-time viewing of the samples from a third party computing device; send a command to the microcontroller via the wireless transceiver to increase the predefined frequency, and output the received samples to the third party computing device upon receipt of the samples from the cardiac monitor. The microcontroller increases the frequency of the transmission upon a receipt of the command.

In an eighth aspect of the present disclosure, which may be combined with any other aspect, or portion thereof, the predefined frequency includes at least one of a time interval and a number of the samples recorded since a previous one of the transmissions.

In a ninth aspect of the present disclosure, which may be combined with any other aspect, or portion thereof, outputting the samples includes creating a graphical representation of the samples.

In a tenth aspect of the present disclosure, which may be combined with any other aspect, or portion thereof, the cardiac monitor transmits each of the samples after that sample is recorded at the increased frequency.

In an eleventh aspect of the present disclosure, which may be combined with any other aspect, or portion thereof, the cardiac monitor does not perform any rhythm or beat detection analysis of the samples prior to transmitting them to the server.

In a twelfth aspect of the present disclosure, which may be combined with any other aspect, or portion thereof, one or more of the applications on one or more of the worker nodes are configured to receive a sequence of values, each of the values representing a time difference between when a cardiac beat of a patient was recorded by a cardiac monitor and when a previous cardiac beat of the patient was recorded by the cardiac monitor; maintain a plurality of encoding tables, each encoding table includes a plurality of codes, each of the codes associated with an upper value threshold and a lower value threshold; process some of the codes in the sequence, including the steps of: select one of the tables for encoding that value based on the previous two codes assigned; and encode that value with one of the codes in the selected table; and store the encoded data in a memory.

In a thirteenth aspect of the present disclosure, which may be combined with any other aspect, or portion thereof, one or more applications on one or more of the nodes are further configured to receive cardiac data of a patient of the patient contemporaneous to the cardiac data; analyze the received cardiac data and generate one or more alerts regarding the patient based on the analysis; identify the alerts as being false based on user input associated with the cardiac data; and pause analysis of further cardiac data of the patient for a predetermined amount of time.

In a fourteenth aspect of the present disclosure, which may be combined with any other aspect, or portion thereof, a method for scalable ECG analysis is provided. The method includes maintaining a plurality of worker nodes and executing on a master node a control plane to spin up and spin down the worker nodes.

The one or more of the nodes are executed by at least one of one or more CPUs and one or more GPUs, each including at least one pod. Each pod is associated with an address and includes one or more containers. Each container includes a run-time environment in which one or more ECG analysis applications are executed and associated with computational resources.

Spinning up the worker nodes uses the computational resources, further including coordinating instantiation and lifecycle of the pods, which includes coordinating execution of the ECG analysis applications associated with the worker nodes, including spinning up the nodes whose output is needed by other ones of the nodes before spinning up the other nodes needing the output, receiving a message regarding completion of the output, and spinning up the other nodes needing the output. Spinning up the other nodes after spinning up the nodes producing the output conserves the computational resources and allows to increase a number of the nodes producing the output that are spun up.

In a fifteenth aspect of the present disclosure, which may be combined with any other aspect, or portion thereof, the worker nodes associated with those of the ECG analysis applications utilizing artificial intelligence are executed by of the one or more of the GPUs.

In a sixteenth aspect of the present disclosure, which may be combined with any other aspect, or portion thereof, the pods communicate with each other via a queuing service.

In a seventeenth aspect of the present disclosure, which may be combined with any other aspect, or portion thereof, spinning down one of the pods includes retaining connection of the node associated with that pod to GPU or CPU executing the node.

In an eighteenth aspect of the present disclosure, which may be combined with any other aspect, or portion thereof, the ECG analysis applications include a beat detector application, a noise detection application, an atrial fibrillation detection application, a premature ventricular contraction detection application, file conversion application for third party analysis applications, and a file combining application that combines the output of other ones of the applications.

In a nineteenth aspect of the present disclosure, which may be combined with any other aspect, or portion thereof, the worker nodes associated with the beat detector application and the noise detection application are spun up before the nodes associated with the atrial fibrillation detection application, the premature ventricular contraction detection application, the file conversion application, and the file combining application.

In a twentieth aspect of the present disclosure, which may be combined with any other aspect, or portion thereof, the method further includes providing a cardiac monitor. The cardiac monitor includes at least one pair of ECG sensing electrodes; an ECG front end circuit interfaced to a microcontroller and configured to capture cardiac action potentials sensed by the pair of ECG sensing electrodes which are output as ECG signals; a wireless transceiver interfaced to the microcontroller; and a memory interfaced to the microcontroller.

The microcontroller is operable to execute under micro programmable control and configured to sample the electrocardiographic signals, to store each of the samples into the memory, and to transmit using the wireless transceiver to a server those of the samples that have not previously been transmitted to the server at a predefined frequency.

The method further includes receiving by one or more of the applications a request for a real-time viewing of the samples from a third party computing device; sending a command to the microcontroller via the wireless transceiver to increase the predefined frequency, wherein the microcontroller increases the frequency of the transmission upon a receipt of the command; and outputting the received samples to the third party computing device upon receipt of the samples from the cardiac monitor.

Additional features and advantages of the disclosed devices, systems, and methods are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment is not required to have all of the advantages listed herein. Moreover, it should be noted that the language used in the specification has been selected for readability and instructional purposes, and not to limit the scope of the present subject matter.

BRIEF DESCRIPTION OF THE DRAWINGS

Understanding that figures depict only typical embodiments of the invention and are not to be considered to limit the scope of the present disclosure, the present disclosure is described and explained with additional specificity and detail through the use of the accompanying figures. The figures are listed below.

FIG. 5 is a routine for monitoring data processing for use in the method of FIG. 2 in accordance with one embodiment.

DETAILED DESCRIPTION

Figure 1:
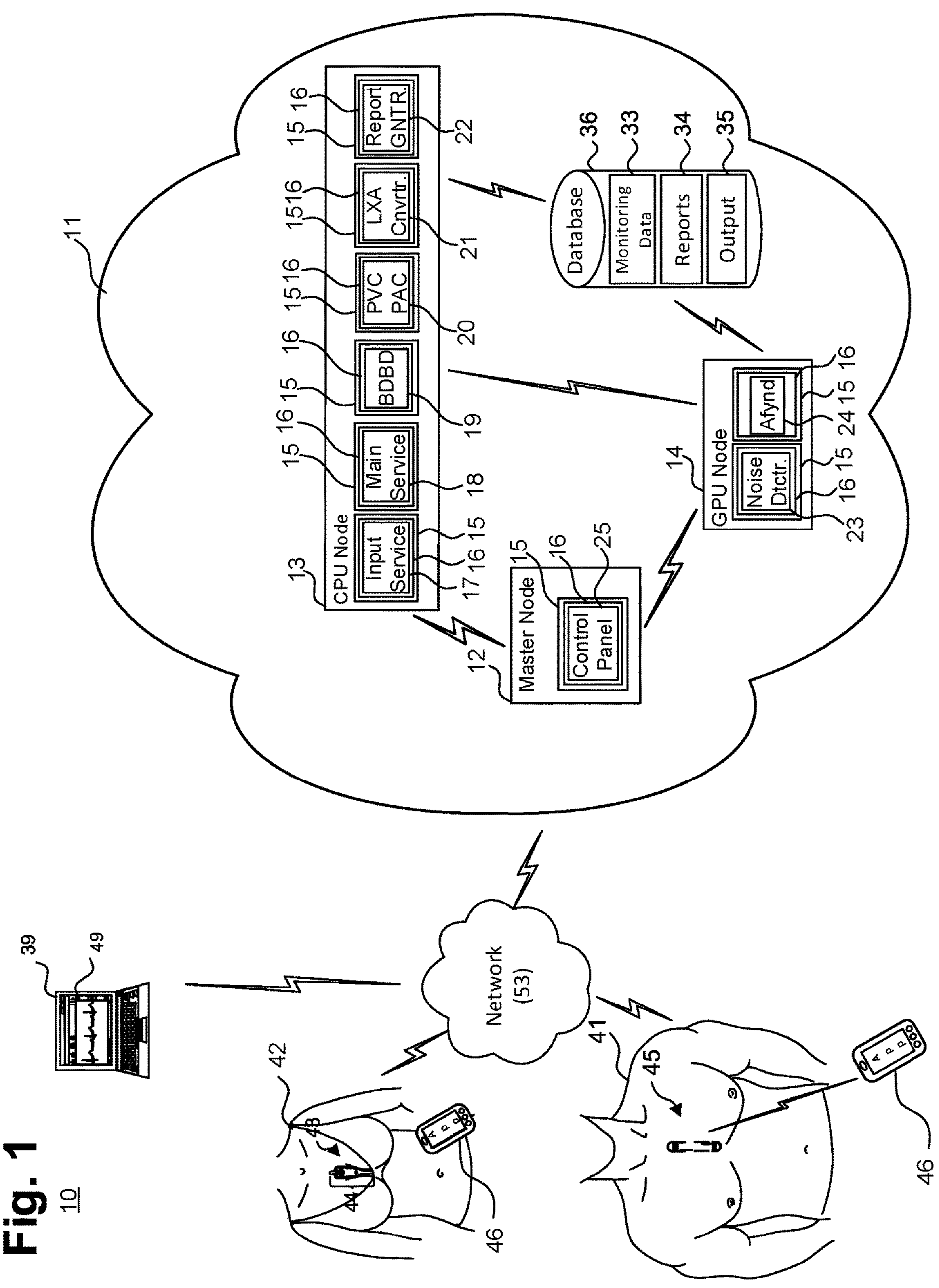
FIG. 1 is a diagram showing a system for scalable ECG analysis in accordance with one embodiment.

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specific the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being “directly on,” “directly engaged to,” “directly connected to,” or “directly coupled to” another element or layer, there may be no intervening elements or layers present. Other words used to describe the relationship between elements should be interpreted in a like fashion (e.g., “between” versus “directly between,” “adjacent” versus “directly adjacent”). As used herein, the term “and/or” includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as “first,” “second,” and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as “inner,” “outer,” “beneath,” “below,” “lower,” “above,” “upper,” and the like, may be used herein for ease of description to describe one element or feature’s relationship to another element(s) or feature(s) as illustrated in the figures. Spatially relative terms may be intended to encompass different orientations of the device in use or operation in addition to the orientation depicted in the figures. For example, if the device in the figures is turned over, elements described as “below” or “beneath” other elements or features would then be oriented “above” the other elements or features. Thus, the example term “below” can encompass both an orientation of above and below. The device may be otherwise oriented (rotated 90 degrees or at other orientations) and the spatially relative descriptors used herein interpreted accordingly.

Efficient use of computational resources can be accomplished by spinning up the ECG analysis applications whose input is necessary for the work of subsequent applications. FIG. 1 is a diagram showing a system 10 for scalable ECG analysis in accordance with one embodiment. The system includes a cloud computing environment 11 within which a cluster of nodes 12-14 are located. In one embodiment, the cloud-computing environment 11 can be implemented as part of Azure Kubernetes Service provided by Microsoft Corporation of Redmond, Washington, though in a further embodiment, other implementations of the cloud-computing environment are possible. Each node 12-14 is one can be a physical computing machine, such as a server. In a further embodiment, each node 12-14 can be a virtual computing machine. The processing in each node 12-14 can be implemented using one or more graphics processing units (“GPUs”), central processing unit (“CPUs”), or a combination of the GPUs and CPUs. Thus, in one embodiment, the node 13 is implemented using one or more CPUs, and the node 14 is implemented using one or more GPUs. The node 12 can be implemented using either CPUs, though in a further embodiment other kinds of processors used to implement the node 12 are also possible. The nodes 13 and 14 are referred to as “worker nodes” while the node 12 is referred to as a “master node”. Each nodes 12-14 further includes one or more pods 15, with each pod including an individually-addressable address being a collection of one or more containers 16, with each container being a run-time environment in which an application 17-25 is executed. Each container 16 is individually addressable with the pod 15 and due to one pod 15 being capable of including multiple containers, multiple copies of the same application 17-25 can be simultaneously executed within a single pod 15. While only a single CPU node 13 and a single GPU node 14 are shown with reference to FIG. 1, the cloud-computing environment could include multiples GPU nodes 14 and CPU nodes 13. Further, while the applications 17-22 are shown as all being executed by a single CPU node 13, a single node 13 could execute only one or a few of these applications 17-22, with multiple nodes 13 being necessary for the execution of all of the applications 17-22. Likewise, the applications 22-23 could be executed on one or multiples GPU nodes 14. The GPU nodes 14 and the CPU nodes 13 are interfaced to a secure database 36 in which the results of the physiological monitoring 33 being analyzed can be stored along with reports 34 generated based on the analysis of the monitoring data 33 as well as the output of the applications being executed in the containers 16. The monitoring data 33 being processed can include cardiac (such as electrocardiographic data) as well as other physiological (such as patient temperature, oxygen saturation, respiration, and blood glucose data), and non-physiological (such as actigraphy) data collected during the monitoring.

The execution of the applications 17-24 on the nodes 13-14 are controlled by a control plane 25 application executed on the master node 12. In particular, the master node 12 controls the spinning up and spinning down of the worker nodes 13-14 when the execution of the applications 17-24 on those nodes 13-14 is necessary for processing incoming monitoring data 33, thus also controlling instantiation and lifecycle of the pods. Spinning up a node 13-14 involves providing the node 13-14 with access to computational resources in the cloud-computing environment 11, such as memory necessary to support the computations of that node 13-14, a particular GPU or CPU that executes that node, or in the case of a node 13-14 including a virtual machine, instantiation of the virtual machine. When a particular node 13-14 is temporarily not needed and is being spun down, instead of being disconnected from the allocated resources, the node 13-14 is put into a “sleep state” in which the node 13-14 retains connection to the allocated resources (including the GPU or CPU executing that node 13-14) to reduce the time that the node needs to spun up again even though the resources are used for some other purpose during the time the node is “asleep.”

The control plane 25 spins up and down the nodes 13-14 based on the order in which their output 35 is needed for processing of monitoring data 33. Thus, the applications executed within containers 16 in pods 15 on the nodes 13-14 can include a beat detector application 19 (“BDBD”) that determines which digitized cardiac signals in the monitoring data 33 correspond to heart beats, derives a heart rate of the patient, and compresses the beats for ease of storage as further described below with reference to FIG. 6; a noise detection application 23; an atrial fibrillation detection application (“afynd”) 24 that detects the patient experiencing atrial fibrillation based on the monitoring data; a premature ventricular contraction detection application (“PVC PAC”) 20 that detects premature ventricular contractions in the monitoring data; a file conversion application that converts the results of the processing of other applications (such as the output 35) into a format suitable for third party analysis (LXA cnvrtr.) 21; and a file combining application that combines the output 35 of other applications into a single report 34 (Report GNTR) 22 that can be stored in the database 36. It should be appreciated that such examples are non-limiting, and thus, for example, additional processes and algorithms may be added the embodiment shown in FIG. 1. Additional algorithms can be added to detect arrhythmias, pauses, tachycardia, and ventricular tachycardia.

The applications further include an input service 17 which handles communication with the device performing the monitoring (such as devices 43, 45 described further below) and third party devices to receive the monitoring data 3: and alter parameters of the monitoring if necessary. The input service 17 can further pause the processing of monitoring data 33 prior to a completion of the monitoring based on the monitoring data 33 triggering false alarms, as further described below. The input service 17 can also communicate with computing devices executing an ECG reading software, such as the software described in U.S. Pat. No. 9,408,551, issued Aug. 9, 2016, the disclosure of which is incorporated by reference The applications further include a main service application 18 that includes a queuing service that enables the transfer of data between different pods 15 that are on the same node 12-14 or on different nods 12-14, allowing the different applications to exchange the results 35 of their processing as well as for the command panel 25 to provide commands and receive responses to the other nodes 13-14. Still other applications are possible.

The control panel 25, the input service 17, and the main service 18 applications are necessary throughout the processing of the monitoring data 33 and are therefore spun up before other applications. The nodes 13-14 for the other applications are spun up in the order the applications on those nodes 13-14 are necessary for processing the data. Thus, because the output 35 of the beat detector application 19 and the noise detection application 23 is necessary for the work of afynd application 24, the PVC PAC application 20, the file conversion application 21, and the file combining application 22, the nodes 13-14 necessary for the execution of the beat detector application 19 and the noise detection application 23 are spun up before the nodes 13-14 associated with the afynd application 24, the premature ventricular contraction detection application 20, the file conversion application 21, and the file combining application 22. As a result, the computation resources necessary for the applications 24, 20, 21, and 22 are not used up before these applications 24, 20, 21, and 22 are actually able to perform their functions. Instead the computational resources are allocated to the applications 19 and 23, allowing to increase the number of instances of the applications 19 and 23 that are processing incoming monitoring data 33 at the same time, and thus allowing to maximize the number of people whose monitoring data 33 is processed at the same time. Once the initial processing by the applications 19 and 23 is complete, the nodes 13-14 for those applications are spun down, allowing to reallocate the computational resources previously dedicated to the applications 19 and 23 to the applications 24, 20, 21, and 22, at which point they can complete the analysis of the monitoring data 33. Thus, the system 10 allows to scale up the number of patients whose monitoring data is being analyzed at the same time within adding computational infrastructure.

While in the description above the output 35 of the analysis of the applications is mentioned as used for creating reports, other uses are possible. For example, the output 35 can include alerts that are provided to the relevant medical personnel reviewing the results of the monitoring and that can take required action to help the patient 41, 42 if necessary. For example, the output 35 of the BDBD application 19 can be an alert that the patient's heart rate exceeds a predefined threshold (such as 90 beats per minute) and that the patient is experiencing a potentially dangerous tachycardia event. Likewise, the afynd application can similarly generate an alert that the patient is experiencing atrial fibrillation. Other alerts by other applications in the cloud-computing environment 11 are possible.

Further, while in the description above, applications with particular functions are mentioned, in a further embodiment, other applications the output 35 of whose processing is necessary for the work of other applications can be spun up before the applications utilizing that output. In particular, while in the description above the applications process cardiac monitoring data, the spinning up and down of applications involved in processing of other kinds of physiological data can be performed based on the order in which the output 35 of those applications is used.

The monitoring data 33 that is processed by the cloud-computing environment 11 can be obtained using either a cutaneous physiological monitor 43 or an implantable monitor 45 implanted into the patient 41, 42. The monitors 43, 45 that collect the data do not perform substantive analysis of the data, such as any rhythm or beat detection analysis of electrocardiography samples prior to transmitting them to the cloud-computing environment 11; all such analysis is performed within the cloud-computing environment 11. Both kinds of monitors 43, 45 can be positioned at the sternal midline 44 of the patient 41, 42, though other kinds of positions are also possible. In one embodiment, the cutaneous monitor can be the cutaneous electrocardiography monitor described in U.S. Pat. No. 9,700,227, issued Jul. 11, 2017, the disclosure of which is incorporated by reference. Briefly, in this embodiment, the monitor 43 components, a flexible extended wear electrode patch and a reusable monitor recorder that removably snaps into a receptacle on the electrode patch. The wearable monitor 43 sits centrally (in the midline) on the patient's chest along the sternum oriented top-to-bottom. The ECG electrodes on the electrode patch are tailored to be positioned axially along the midline of the sternum for capturing action potential propagation in an orientation that corresponds to the aVF lead used in a conventional 12-lead ECG that is used to sense positive or upright P-waves. Operation of the circuitry of the monitor recorder is managed by a microcontroller that includes a program memory unit containing internal flash memory that is readable and writeable and that operates under modular micro program control as specified in firmware stored in the internal flash memory. The microcontroller connects to the ECG front end circuit of the recorder that measures raw cutaneous electrical signals through the electrodes provided on the disposable patch and measures samples of ECG signals acquired by the front end circuit. The microcontroller acquires, samples, digitizes, signal processes, and store digitized ECG data into available storage locations in the memory of the monitor recorder. The circuitry of the monitor further includes a wireless transceiver interfaced to the microcontroller through which the microcontroller can offload the collected data 33. The cutaneous monitor can record electrocardiography data, other physiological data, and non-physiological data such as actigraphy data. In a further embodiment, other kinds of cutaneous monitors 43 are possible.

In one embodiment, the implantable monitor 45 can be the implantable medical device described in U.S. Patent Application Publication No. 2021/0000345A1, published Jan. 7, 2021 and issued as U.S. Pat. No. 11,696,681, the disclosure of which is incorporated by reference, though in a further embodiment, other implantable monitors are possible. Briefly, a housing of the implantable medical device includes a hollow body forming a first electrode on an outer surface with end caps affixed to opposite ends, one such end cap forming a second electrode on an outer surface. A microcontroller circuit (also referred to as a microcontroller) is provided circumferentially within the housing and includes a microcontroller operable under program instructions stored within a non-volatile memory device. An analog front end is electrically interfaced to the first and the second electrodes and is operable to sense electrocardiographic signals. A transceiver circuit is operable to wirelessly communicate with an external data device such as the cloud-computing environment 11. The program instructions define instructions for the microcontroller to continuously sample the electrocardiographic signals into the non-volatile memory device and to offload the non-volatile memory device to the external data device via the transceiver circuit. A receiving coil and a charging circuit are operable to charge an onboard power source for the microcontroller circuit. The implantable monitor can record electrocardiography data, other physiological data, and non-physiological data such as actigraphy data. In a further embodiment, other kinds of implantable monitors 45 are possible.

The monitors 43, 45 can communicate with the cloud-computing environment 11 through a network 53, such as the Internet or a cellular network. The communication of the monitors 43, 45 with the network 53 can be direct if the wireless transceivers of the monitors 43, 45 are capable of directly contacting the network, such as if the wireless transceivers include cellular chipsets as described in U.S. Pat. No. 10,667,711, issued Jun. 2, 2020, the disclosure of which is incorporated by reference. Alternatively, the wireless transceivers of the monitors 43, 45 can offload the monitoring data 33 to an intermediary device, such as a mobile phone 46 executing a mobile application (though other intermediary devices are possible), which in turn provides via the network 53 the monitoring data 33 to the cloud-computing environment.

Under most circumstances, the monitor 43, 45 offloads the monitoring data 33 to the cloud-computing environment 11 using the wireless transceiver with a predefined frequency. Such frequency can be defined either in terms of time (such as transmitting all the data collected 33 in the last minute, hour, day, or another time interval) or in terms of the amount of data 33 (such as a number of electrocardiographic samples) recorded since the last transmission to the cloud-computing environment, such as making a transmission after a certain number of samples of electrocardiographic samples has been recorded since the last transmission. The frequency of transfer is limited by the power consumption of such transfer, with the more frequent transfer draining the power of the monitor 43, 45 quicker. The predefined frequency can be preprogrammed into the microcontroller of the monitor 43, 45 before the monitoring begins, being part of the firmware under whose control the microcontroller operates. However, if an alert that is part of an output 35 generated based on processing of the monitoring data 33 indicates that the patient is experiencing an episode of cardiac condition and a medical professional (such as a physician, though in a further embodiment, other medical professionals are possible) wants to examine the data at more frequent intervals (such as at near-real-time, though other frequencies are possible), the frequency of the data 33 transmission can be increased. Alternatively, the medical professional can initiate the request for an increase in the frequency of the data transmission even without an alert being generated. Thus, upon receiving a request from a computing device 39 associated with the medical professional reviewing results of processing of the data 33, the input service 17 can send a signal via the network 53 to the wireless transceiver of the monitor 43, 45, which the wireless transceiver provides to the microcontroller of the monitor 43, 45. The signal commands the microcontroller to increase the frequency with which the monitoring data 33 is offloaded to the cloud-computing environment 11. In one embodiment, the signal commands the microcontroller of the monitor 43, 45 to increase the rate the monitoring data 33 is offloaded to a near-real-time level, with a sample of the monitoring data 33 being offloaded as soon as the sample is written into the memory of the monitor 43, 45 (or every second). In a further embodiment, other increased frequency of providing the data 33 by the monitor 43, 45 to the cloud-computing environment is possible. The monitor 43, 45 continues to provide the monitoring data 33 at the increased frequency until a further signal is received from the input service 17 via the network 54 to return to the previous frequency of data 33 transmission. The input service 17 sends the signal to return the transmission of the data 33 to the preset frequency in response to receiving from the computing device 39 associated with the medical professional a message that the increased rate of data transmission is no longer necessary (which can be based on a specific command from the medical professional or the medical professional simply closing the application 49 the results of the data processing). In a further embodiment, if no signal to return to the previous frequency of transmission is received from the input service 17, the monitor 43, 45 can automatically return to the preset frequency of providing the data 33 to the cloud-computing environment 11 upon an expiration of a predefined time period since the receipt of the signal to increase the frequency of the transmission. The return to the lower, preset level of data 33 transfer to the cloud-computing environment 11 allows to conserve the power of the monitor 33 when the increased level of transmission is no longer necessary.

Upon receipt of the data 33 by the input service 17, the input service 17 outputs the data 33 in graphical form to the medical professional who requested the data via the computing device 39 associated with the medical professional. In one embodiment, the input service 17 can create an electrocardiograph or another graphical representation of the data 33 as soon as that data is received and provide the graphical representation via the network 53 to the application 49 running on the computer device 39 associated with the medical professional. Thus, if the monitor 43, 45 transmits the recorded data 33 every second, the input service 17 prepares a portion of the graphical representation corresponding to the newly received data and transmits the graphical representation to the computing device 39 via the network 53, with the application 49 on the device displaying the newly received graphical representation along with at least a portion of the graphical representation of the data 33 received earlier. Thus, the medical professional is provided a view of the patient's physiology over time (such as an electrocardiograph) that is updated in near-real-time, allowing the medical professional to observe the patient's condition as the condition evolves over time. In a further embodiment, instead of preparing the graphical representation, the input service 17 only forwards to the application 49 running on the computing device 39 the received monitoring data 39, with the application 49 preparing and outputting on the computing device 39 the graphical representation of the received data. In a further embodiment, in addition to the graphical representation of the received data, the input service 17 can further provide to the application 49 on the computing device 39 outputs 35 of other applications in the cloud-computing environment as those outputs 35 become available.

While in the case above a medical professional needs to see the graphical representation of the data 33 as soon as possible when the patient 41, 42 is experiencing a cardiac condition, in other cases, an alert that is part of an output 35 regarding the patient experiencing a cardiac condition such as tachycardia may be generated due to non-medical reasons, such as the patient engaging in strenuous exercise. If the non-medical reasons persist for an extended time, as is common when someone engages in physical exercise, then repeated alerts will be generated and provided to the medical professional, thus needlessly distracting the medical professional and delaying the medical professional from evaluating the conditions of patients truly experiencing episodes of cardiac conditions. Accordingly, to prevent such situation, the cloud-computing environment 11 performs a secondary analysis of the monitoring data 33 based on which an alert is generated to verify that an alert is not false. In one embodiment, the secondary analysis is performed by the input service 17, though in a further embodiment, another application in the cloud-computing environment 11 can perform the analysis. As the monitoring data 33 can include actigraphy data, the secondary analysis can include identifying the actigraphy data contemporary to the physiological data on which the alert is based to identify if there is a non-medical reason (such as the patient exercising) for an alert to be false (not indicative of the patient 41, 42 experiencing a medical condition). For example, if the secondary analysis indicates that the patient 41, 42 is exercising at the time the physiological data indicative of a medical condition (such as tachycardia) was recorded, the output of the secondary analysis will be that the alert is false. In one embodiment, the output of the secondary analysis by one of the applications is enough to declare an alert as false. In a further embodiment, a confirmation from a medical professional that the alert is false needs to be received by the cloud-computing environment before the alert is declared false. While in the description above actigraphy data is described as used for the declaration of an alert as false, in a further embodiment, other kinds of non-physiological data can be used for declaration of an alert based on contemporaneous physiological data as false.

Once the input service 17 (or another part of the cloud-computing environment 11) identifies an alert as false, the input service 17 (or another part of the cloud-computing environment 21) messages the remaining applications analyzing the data 33 of the patient to stop generating further alerts for a predefined "pause" period, such as one to three hours, though in a further embodiment, other time intervals are possible. In a further embodiment, the alerts can still be generated by the relevant applications in the cloud computing environment 11 during the pause period, but are not forwarded to any medical professionals (though are available for later review). In one embodiment, if the time the data 33 based on which the alert was generated was recorded is available, the pause period runs from the time the data 33 was recorded. Alternatively, or if the time the data was recorded is not available, the pause period runs from the time the alert was generated. By instituting a pause period following a false alert, the cloud-computing environment 11 conserves the computational resources necessary for the generation and delivery of alerts as well as avoids unnecessarily distracting the medical professional to whom the alerts are provided.

Figure 2:
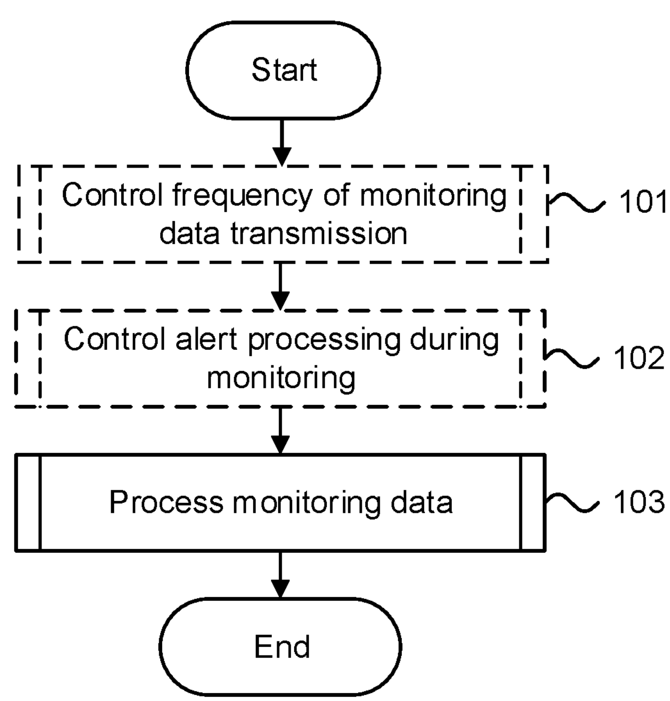
FIG. 2 is a flow diagram showing a method for scalable ECG analysis in accordance with one embodiment.

Efficient use of computational resources as well as improved control over how often the monitoring data 33 is provided and how often that data is processed allows to improve the speed and quality of analysis of ECG and other physiological data. FIG. 2 is a flow diagram showing a method 100 for scalable ECG analysis in accordance with one embodiment. The method 100 can be performed using the system 10 of FIG. 1. Optionally, frequency of monitoring data 33 transmission is controlled, as further described below with reference to FIG. 3 (step 101). Optionally, alert processing during monitoring is controlled, as further described with reference to FIG. 4 (step 102). The monitoring data 33 is processed, as further described below with reference to FIG. 5 (step 103), ending the method 100. While step 103 is shown as occurring after steps 101 and 102, the step 103 can also occur before and at the same time as steps 101 and 102.

Figure 3:
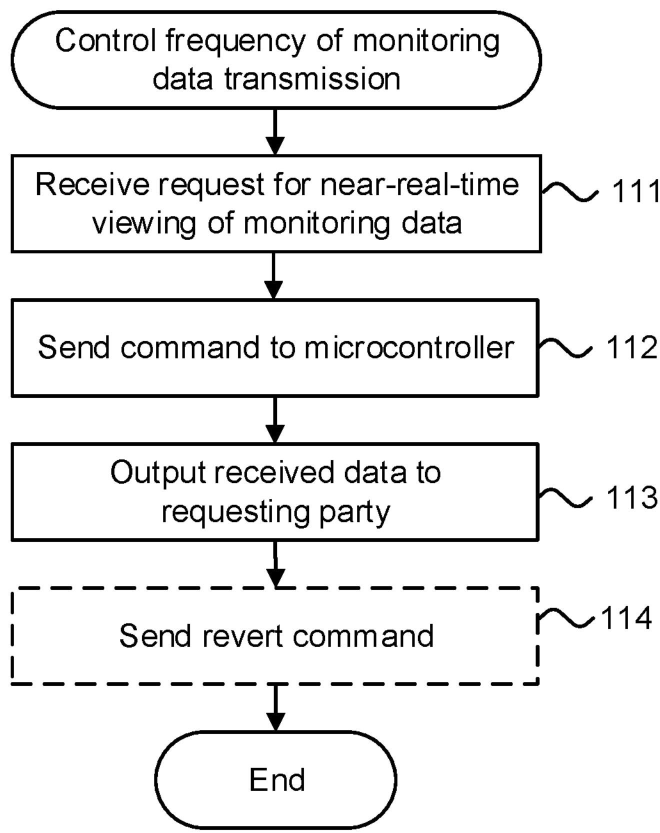
FIG. 3 is a flow diagram showing a routine for controlling frequency of monitoring data transmission for use in the method of FIG. 2 in accordance with one embodiment.

Controlling frequency at which the monitor 43, 45 performs transmission of the monitoring data 33 to the cloud-computing environment 11 allows to provide to a physician evaluating the patient's condition the most-up-to-date information at the time that information is needed most. FIG. 3 is a flow diagram showing a routine 110 for controlling frequency of monitoring data 33 transmission for use in the method 100 of FIG. 2 in accordance with one embodiment. A request for near-real-time viewing of monitoring data 33 is received by the input service 17 of the cloud-computing environment 11 from a computing device 39 associated with the medical professional evaluating the patient (step 111). In one embodiment, the request can be received based on alert generated as part of the output 35 of one of the applications of the cloud-computing environment 11. Alternatively, the request can be initiated by the medical professional without any alerts being generated by the applications of the cloud-computing environment 11. In a further embodiment, instead of a near-real-time viewing, the medical professional can request another frequency of update of the data displayed on the application 49 of the computing device 39.

After the request is received from the computing device 39, the input service 17 of the cloud computing environment 11 provides via the network 53 and the wireless transceiver of the monitor 43, 45 a command to the microcontroller of the monitor to increase the frequency of the transmission of the monitoring data 33 to a near-real-time level (or another level specified in the request), with each sample of the data 33 being transmitted to the cloud-computing environment 11 immediately after the recordation of that data sample 33 into the memory of the monitor 43, 45 (or at another frequency specified by the request) (step 112).

The monitoring data 33 received from the monitor 43, 45 is output via the network 53 by the input service 17 to the computing device 39 (step 113). As described above, the output is of the data can be done in graphical form, with the graphical representation of the data 33 being prepared by the input service 17 or the application 49.

Optionally, the input service 17 sends a command to the monitor 43, 45 via the network 53 to revert to transmitting the data 33 at the earlier, preset frequency (step 114), ending the routine 110. The input service 17 can send the revert command upon receiving a message from the computing device 39 that the near-real-time viewing is no longer necessary. Alternatively, the input service 17 can send the command after an expiration of a predefined time period after the initial command to increase the frequency of the transmission of the data 53 is sent to the monitor 43, 45. In a further embodiment, no revert command is sent to the monitor 43, 45 and the monitor 43, 45 automatically reverts to the preset data 33 transmission frequency rate upon the expiration of time period following the receipt of the command to increase the frequency, with the length of the time period being predefined in the firmware that controls the microcontroller.

Figure 4:
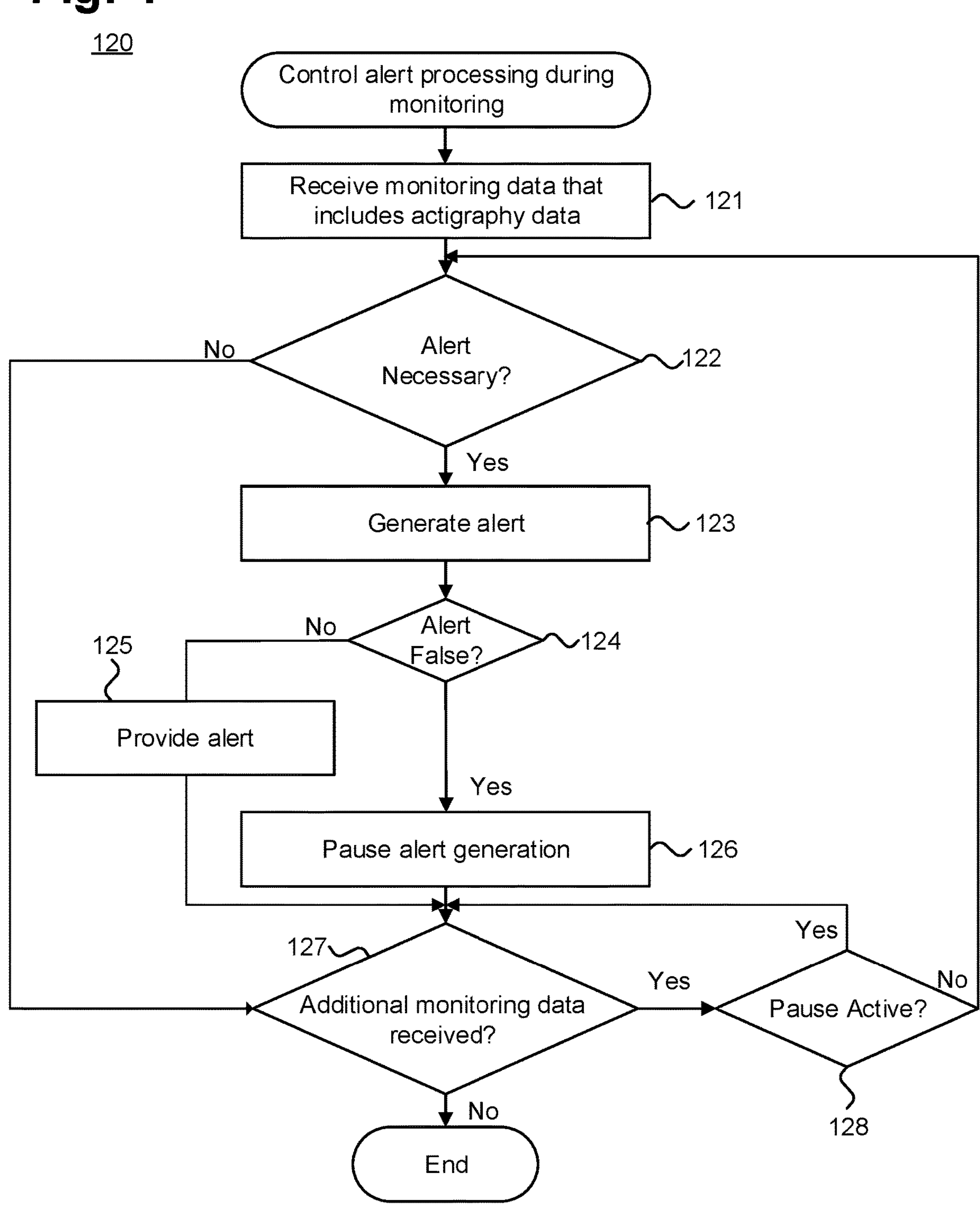
FIG. 4 is a flow diagram showing a routine for controlling alert processing during monitoring for use in the method of FIG. 2 in accordance with one embodiment.

While alerts can initiate the increase of frequency of monitoring data, false alerts can also be a drain on both the computational resources necessary to generate and send them. FIG. 4 is a flow diagram showing a routine 120 for controlling alert processing during monitoring for use in the method 100 of FIG. 2 in accordance with one embodiment. The routine takes place before all of the monitoring data 120 from a particular physiological monitoring of a patient is received by the cloud-computing environment 11, with the data 33 being received in portions. Initially, a portion of the monitoring data 33 that includes physiological (such as electrocardiography) data and actigraphy data is received from the monitor 43, 45 by the cloud-computing environment 11 (step 121). If an alert regarding the patient experiencing an episode of a potentially dangerous condition is determined necessary based on the received data 33 (step 122), the alert is generated by the application that made the determination (step 123). If no alert is necessary (step 122), the routine 120 moves to step 127. Whether the alert is false is analyzed, either by the input service 17 or another application, using the actigraphy data as described above, and possibly by requesting a user confirmation of the falseness, and if the alert is false (step 124), alert generation is paused for a predefined period of time (step 126) and the routine 120 moves to step 127. If the alert is not false (step 124), the alert is provided to the medical professional monitoring the patient's 41, 42 condition (step 125) and the routine 120 moves to step 127.

If additional monitoring data 33 is received for that patient 41, 43 (step 127) and the alert generation pause period is active, no alerts are generated for the newly-received data 33 and the routine 120 returns to step 127 to check whether still additional data 33 is received. If additional monitoring data 33 is received for that patient 41, 43 (step 127) and the alert generation pause period is not active, the routine 120 returns to step 122. If no additional data 33 is received (step 127), the routine 120 ends.

As mentioned above, in a further embodiment, during the alert pause period, an alert may still be generated but not provided to the medical professional reviewing the data. Further, though the data 33 that triggers the alert pause period must include actigraphy (or some other data that can provide context for the physiological data based on which the alert can be declared false), the subsequent data for which no alerts may be generated due to the alert pause period can only include the physiological data that may serve as grounds for an alert.

Spinning up those of the nodes 13-14 whose output 35 is needed by other nodes 13-14 prior to those of the nodes needing the output 35 allows to increase the amount of monitoring data 33 that can be processed in a particular time period without having to increase the amount of computational resources allocated to such processing. FIG. 5 is a routine 130 for monitoring data processing for use in the method 100 of FIG. 2 in accordance with one embodiment. Monitoring data is received by the cloud-computing environment 11 (step 131) and the control plane 25 executed on the node 12 spins up the worker nodes 13-14 whose output is necessary for other workers nodes 13-14 to perform analysis (steps 132), which starts the execution of the applications on those nodes 13-14. Such nodes 13-14 can include the nodes 13-14 necessary for the execution of the beat detection application 19 and the noise detection application 23, with the function of the beat detection application including performing beat compression as described further below with reference to FIG. 6. The control plane 25 detects the completion of the output 35 of these applications (step 133) and spins the nodes 13-14 of these initial applications down (step 134), thus allowing for reallocation of the computational resources dedicated to these nodes 13-14. The worker nodes 13-14 that need the output 35 of the applications spun up in step 132 are spun up (step 135). Such nodes 13-14 can include the nodes 13-14 on which of atrial fibrillation detection application 24, the PVC PAC application 20, the file conversion application 21, and the file combining application 22 are executed. The completion of the output 35 of the applications executing on the nodes spun up in step 135 is detected by the master plane 25 (step 136) and the master plane 25 spins down the nodes 13-14 spun up in step 135 (step 137). If no more monitoring data 33 remains unprocessed (step 138), the routine 130 ends. If additional monitoring data 33 remains (step 138), the routine 130 returns to step 132.

As mentioned above, nodes 13 necessary for the execution of the input service 17 and the main service application 18 are spun up by the control panel 25 as soon as the control panel 25 starts executing and before monitoring data is received.

Figure 6:
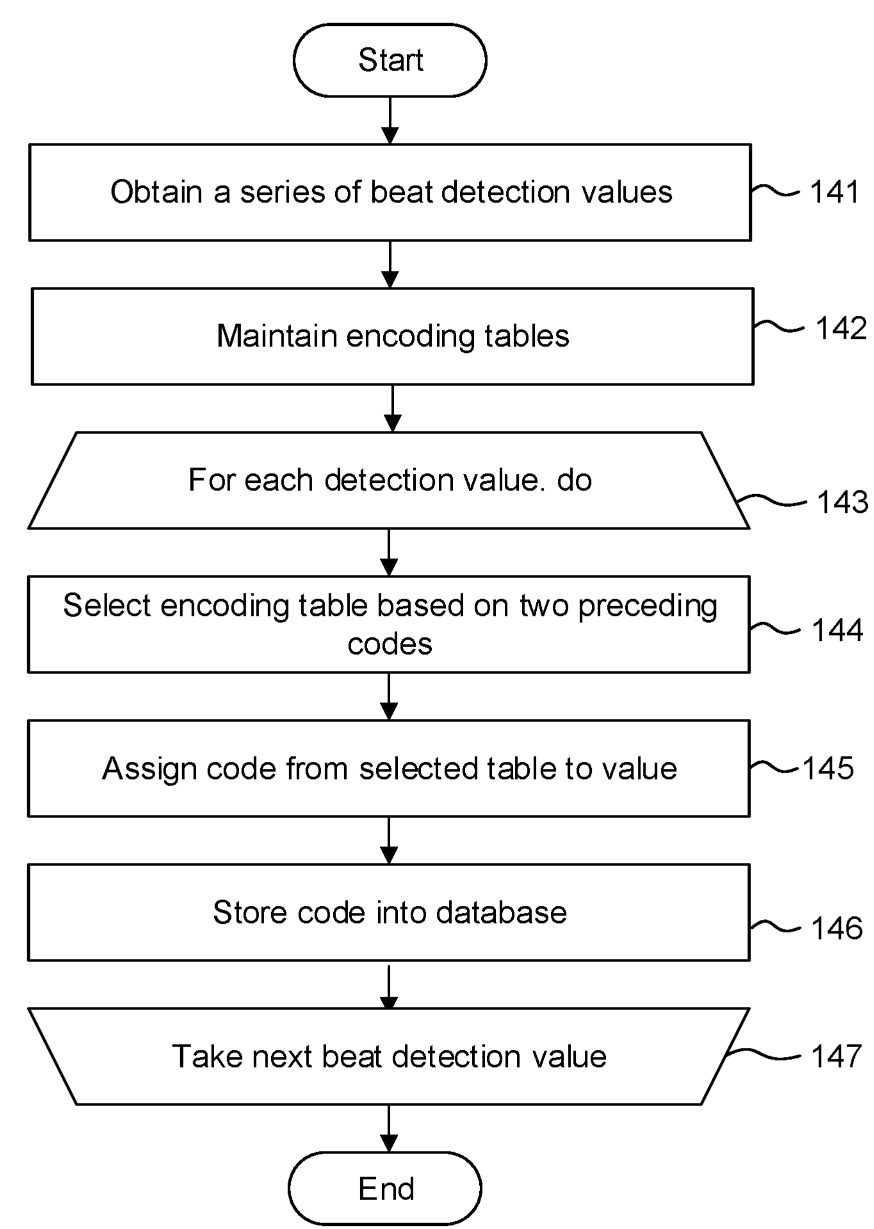
FIG. 6 is a flow diagram showing a subroutine for compressing detected cardiac beats as performed by a beat detection application spun up as described with reference to routine of FIG. 5 in accordance with one embodiment.

Compressing detected beats allows to conserve the memory space and reduce data transmission cost within the cloud-computing environment 11 and allows to use such memory spaces for the functioning of the nodes 12-15. FIG. 6 is a flow diagram showing a subroutine 140 for compressing detected cardiac beats as performed by a beat detection application 19 spun up as described with reference to routine 130 of FIG. 5 in accordance with one embodiment. A sequence of values is obtained by the beat detection application 19 (step 141), such as through previous processing of the monitoring data 33, each of the values representing a time difference between when a cardiac beat of a patient was recorded by a cardiac monitor 43, 45 and when a previous cardiac beat of the patient was recorded by the cardiac monitor. A plurality of encoding tables are maintained by the application 19 (such as in the database 36 or another memory within the cloud-computing environment 11), each encoding table including a plurality of codes, each of the codes associated with an upper value threshold and a lower value threshold (step 142). An iterative processing loop (steps 143-147) is started (step 143) to process each value in turn, proceeding as follows: one of the tables for encoding that value is selected based on the combination of the previous two values that were processed in the sequence (step 144); one table exists for each possible combination, but to reduce the number of tables needed the two previous values are divided by a certain quantization factor before using them to select a table; then, the current value is coded with one of the codes in the selected table, the value falling between the upper and lower threshold of the code with which that value is coded (step 145); the value is encoded into the database 36 as part of the output 35 of the application 19 (step 146) and the loop moves to the next value (step 147). The subroutine 140 ends once all of the values in the sequence have been processed. For the first two values in the sequences (with the first value missing both of two previous values and the second value missing a single previous value), the non-existent previous values needed as input for step 144 are taken to be 0, though in a further embodiment, other numerical values could be used as long as they are consistently used between different iterations of the subroutine 140.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for scalable ECG analysis, comprising:

a plurality of nodes, one or more of the nodes executed by at least one of one or more CPUs and one or more GPUs, the plurality of nodes further comprising:

a plurality of worker nodes, each comprising one or more containers, each container having an address and comprising a run-time environment in which one or more ECG analysis applications are executed and associated with computational resources; and a master node comprising a control plane configured to spin up and spin down the worker nodes, wherein spinning up the worker nodes uses the computational resources, the master node further configured to coordinate instantiation and lifecycle of the one or more containers, which comprises coordinating execution of the ECG analysis applications associated with the worker nodes, comprising spinning up the nodes whose output is needed by other ones of the nodes before spinning up the other nodes needing the output, receiving a message regarding completion of the output, and spinning up the other nodes needing the output, wherein spinning up the other nodes after spinning up the nodes producing the output conserves the computational resources and allows to increase a number of the nodes producing the output that are spun up, wherein one or more applications on one or more of the nodes is configured to:

receive cardiac data of a patient of the patient contemporaneous to the cardiac data;

analyze the received cardiac data and generate one or more alerts regarding the patient based on the analysis;

identify the alerts as being false based on user input associated with the cardiac data; and pause analysis of further cardiac data of the patient for a predetermined amount of time.

2. The system according to claim 1, wherein the nodes associated with those of the ECG analysis applications utilizing artificial intelligence are executed by of the one or more of the GPUs.

3. The system according to claim 1, wherein the one or more containers communicate with each other via a queuing service.

4. The system according to claim 3, wherein spinning down one of the containers comprises retaining connection of the node associated with that container to GPU or CPU executing the node.

5. The system according to claim 1, wherein the ECG analysis applications comprise a beat detector application, a noise detection application, an atrial fibrillation detection application, and a premature ventricular contraction detection application, file conversion application for third party analysis applications, and a file combining application that combines the output of other ones of the applications.

6. The system according to claim 5, wherein the nodes associated with the beat detector application and the noise detection application are spun up before the nodes associated with the atrial fibrillation detection application, the premature ventricular contraction detection application, the file conversion application, and the file combining application.

7. The system according to claim 1, further comprising:

a cardiac monitor, comprising:

at least one pair of ECG sensing electrodes;

an ECG front end circuit interfaced to a microcontroller and configured to capture cardiac action potentials sensed by the pair of ECG sensing electrodes which are output as ECG signals;

a wireless transceiver interfaced to the microcontroller;

a memory interfaced to the microcontroller; and the microcontroller operable to execute under micro programmable control and configured to sample the electrocardiographic signals, to store each of the samples into the memory, and to transmit using the wireless transceiver to a server those of the samples that have not previously been transmitted to the server at a predefined frequency;

one or more of the applications on one or more of the worker nodes configured to:

receive a request for a real-time viewing of the samples from a third party computing device;

send a command to the microcontroller via the wireless transceiver to increase the predefined frequency, wherein the microcontroller increases the frequency of the transmission upon a receipt of the command; and output the received samples to the third party computing device upon receipt of the samples from the cardiac monitor.

8. The system according to claim 7, wherein the predefined frequency comprises at least one of a time interval and a number of the samples recorded since a previous one of the transmissions.

9. The system according to claim 7, wherein outputting the samples comprises creating a graphical representation of the samples.

10. The system according to claim 7, wherein the cardiac monitor transmits each of the samples after that sample is recorded at the increased frequency.

11. The system according to claim 10, wherein the cardiac monitor does not perform any rhythm or beat detection analysis of the samples prior to transmitting them to the server.

12. The system according to claim 1, one or more of the applications on one or more of the worker nodes configured to:

receive a sequence of values, each of the values representing a time difference between when a cardiac beat of a patient was recorded by a cardiac monitor and when a previous cardiac beat of the patient was recorded by the cardiac monitor;

maintain a plurality of encoding tables, each encoding table comprising a plurality of codes, each of the codes associated with an upper value threshold and a lower value threshold;

process some of the codes in the sequence, comprising the steps of:

select one of the tables for encoding that value based on the previous two codes assigned;

and encode that value with one of the codes in the selected table; and store the encoded data in a memory.

13. A method for scalable ECG analysis, comprising:

maintaining a plurality of worker nodes, one or more of the nodes executed by at least one of one or more CPUs and one or more GPUs, each comprising one or more containers, each container having an address and comprising a run-time environment in which one or more ECG analysis applications are executed and associated with computational resources; and executing on a master node a control plane to spin up and spin down the worker nodes, wherein spinning up the worker nodes uses the computational resources, further comprising coordinating instantiation and lifecycle of the one or more containers, which comprises coordinating execution of the ECG analysis applications associated with the worker nodes, comprising spinning up the nodes whose output is needed by other ones of the nodes before spinning up the other nodes needing the output, receiving a message regarding completion of the output, and spinning up the other nodes needing the output, wherein spinning up the other nodes after spinning up the nodes producing the output conserves the computational resources and allows to increase a number of the nodes producing the output that are spun up, wherein one or more applications on one or more of the nodes is configured to:

receive cardiac data of a patient of the patient contemporaneous to the cardiac data;

analyze the received cardiac data and generate one or more alerts regarding the patient based on the analysis;

identify the alerts as being false based on user input associated with the cardiac data; and pause analysis of further cardiac data of the patient for a predetermined amount of time.

14. The method according to claim 13, wherein the worker nodes associated with those of the ECG analysis applications utilizing artificial intelligence are executed by of the one or more of the GPUs.

15. The method according to claim 13, wherein the one or more containers communicate with each other via a queuing service.

16. The method according to claim 15, wherein spinning down one of the containers comprises retaining connection of the node associated with that container to GPU or CPU executing the node.

17. The method according to claim 13, wherein the ECG analysis applications comprise a beat detector application, a noise detection application, an atrial fibrillation detection application, and a premature ventricular contraction detection application, file conversion application for third party analysis applications, and a file combining application that combines the output of other ones of the applications.

18. The method according to claim 17, wherein the worker nodes associated with the beat detector application and the noise detection application are spun up before the nodes associated with the atrial fibrillation detection application, the premature ventricular contraction detection application, the file conversion application, and the file combining application.

19. The method according to claim 13, further comprising: providing a cardiac monitor, comprising:

at least one pair of ECG sensing electrodes;

an ECG front end circuit interfaced to a microcontroller and configured to capture cardiac action potentials sensed by the pair of ECG sensing electrodes which are output as ECG signals;

a wireless transceiver interfaced to the microcontroller;

a memory interfaced to the microcontroller; and the microcontroller operable to execute under micro programmable control and configured to sample the electrocardiographic signals, to store each of the samples into the memory, and to transmit using the wireless transceiver to a server those of the samples that have not previously been transmitted to the server at a predefined frequency;

receiving by one or more of the applications a request for a real-time viewing of the samples from a third party computing device;

sending a command to the microcontroller via the wireless transceiver to increase the predefined frequency, wherein the microcontroller increases the frequency of the transmission upon a receipt of the command; and outputting the received samples to the third party computing device upon receipt of the samples from the cardiac monitor.

* * * * *